United States Patent [19]

Pegnim et al.

[11] 4,050,079
[45] Sept. 20, 1977

[54] ELECTROCARDIOGRAPHIC APPARATUS WITH RECORDING PEN PROTECTOR

[75] Inventors: Timothy C. Pegnim, Wilton, Conn.; Larry R. France, Ossining, N.Y.; John G. Sherman, Yonkers, N.Y.; Claude MacQuignon, Lake Peekskill, N.Y.

[73] Assignee: Cambridge Instrument Company, Inc., Ossining, N.Y.

[21] Appl. No.: 721,873

[22] Filed: Sept. 9, 1976

[51] Int. Cl.² ............... G01D 15/00; G01D 9/00; A61B 5/04

[52] U.S. Cl. ............... 346/145; 346/68; 128/2.06 E

[58] Field of Search ............... 346/33 ME, 68, 136, 346/145; 128/2.06 E

[56] References Cited

U.S. PATENT DOCUMENTS

| | | |
|---|---|---|
| 3,082,970 | 3/1963 | Rasmussen ............... 346/136 X |
| 3,216,021 | 11/1965 | Stefansson ............... 346/136 |
| 3,266,048 | 8/1966 | Schweitzer ............... 346/145 X |
| 3,389,402 | 6/1968 | Rosmanith ............... 346/145 UX |
| 3,922,686 | 11/1975 | France et al. ............... 346/33 ME |

Primary Examiner—George H. Miller, Jr.
Attorney, Agent, or Firm—Eugene E. Geoffrey, Jr.

[57] ABSTRACT

Electrocardiographic apparatus wherein said apparatus is contained within a wholly insulated enclosure and the recording assembly including writing pens is provided with means for placing an insulating barrier in a position to protect the pens when replenishing the recording paper.

8 Claims, 13 Drawing Figures

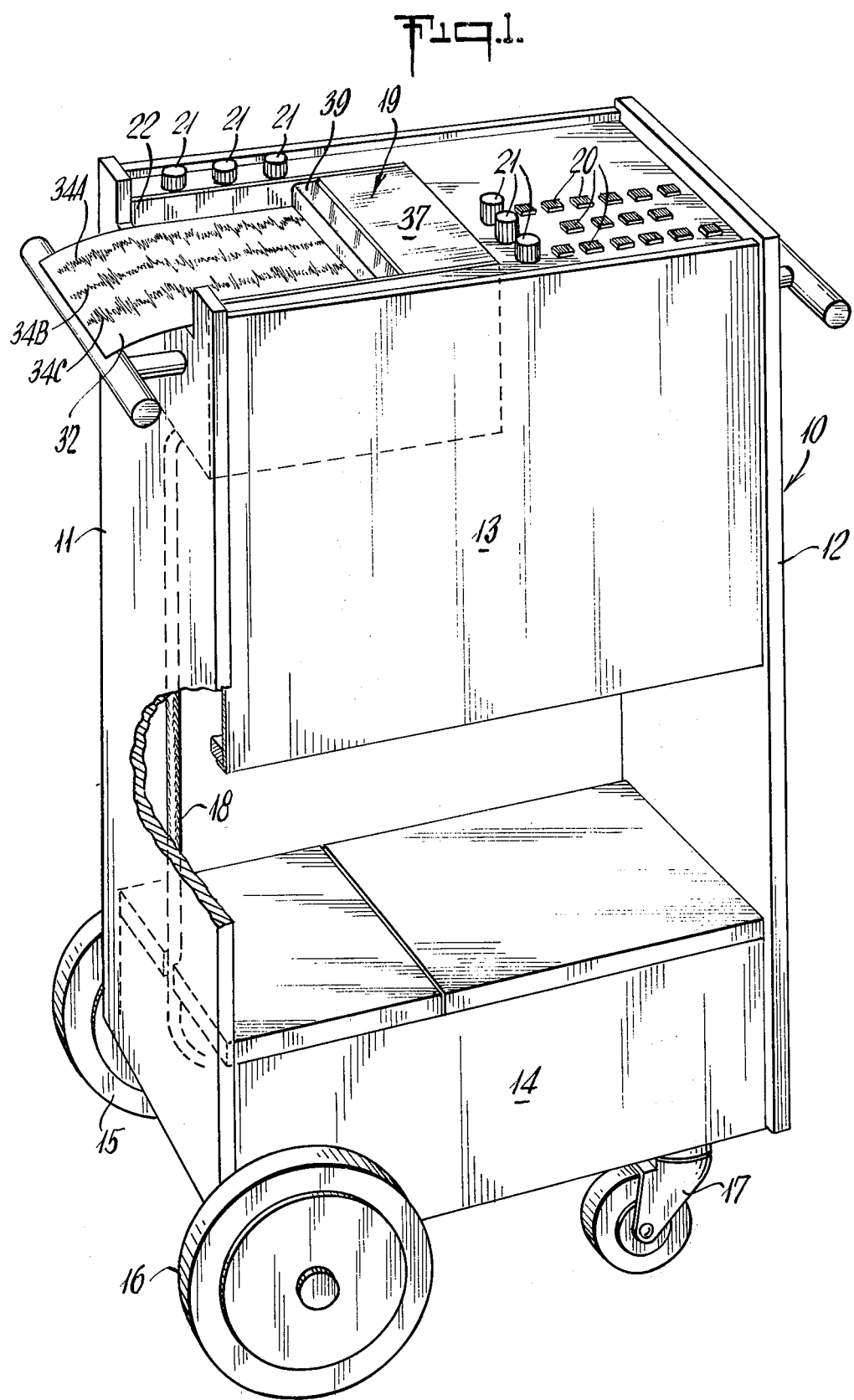

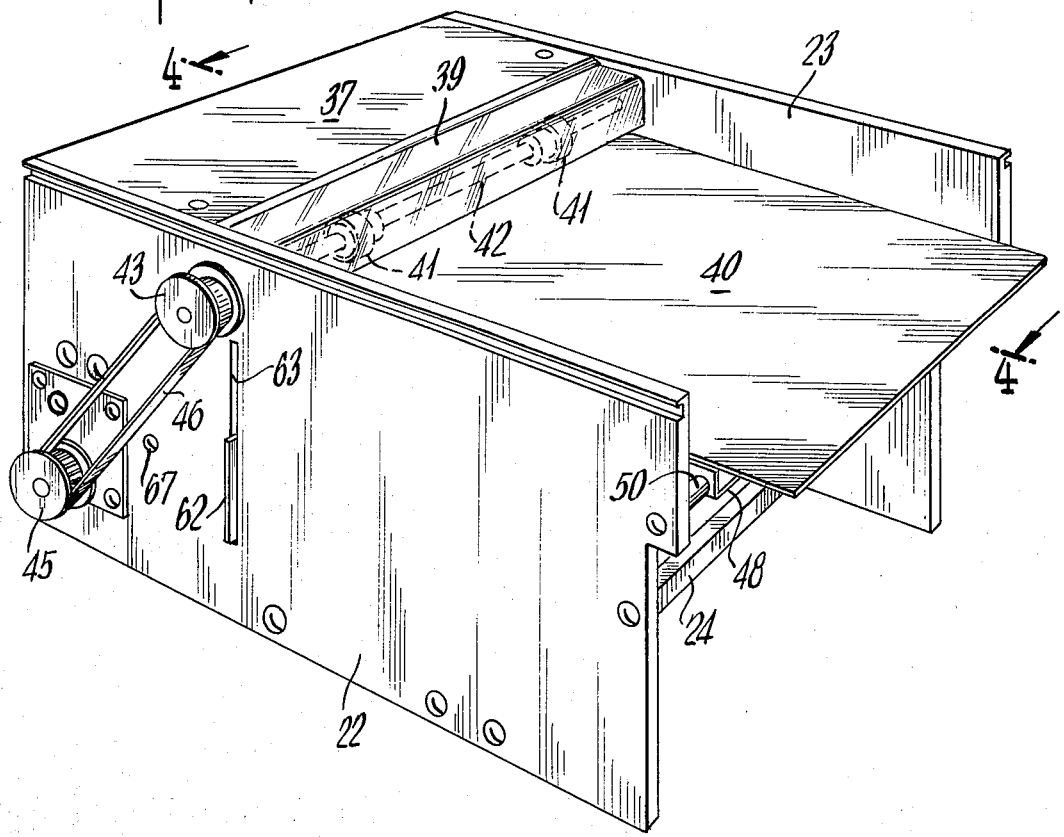
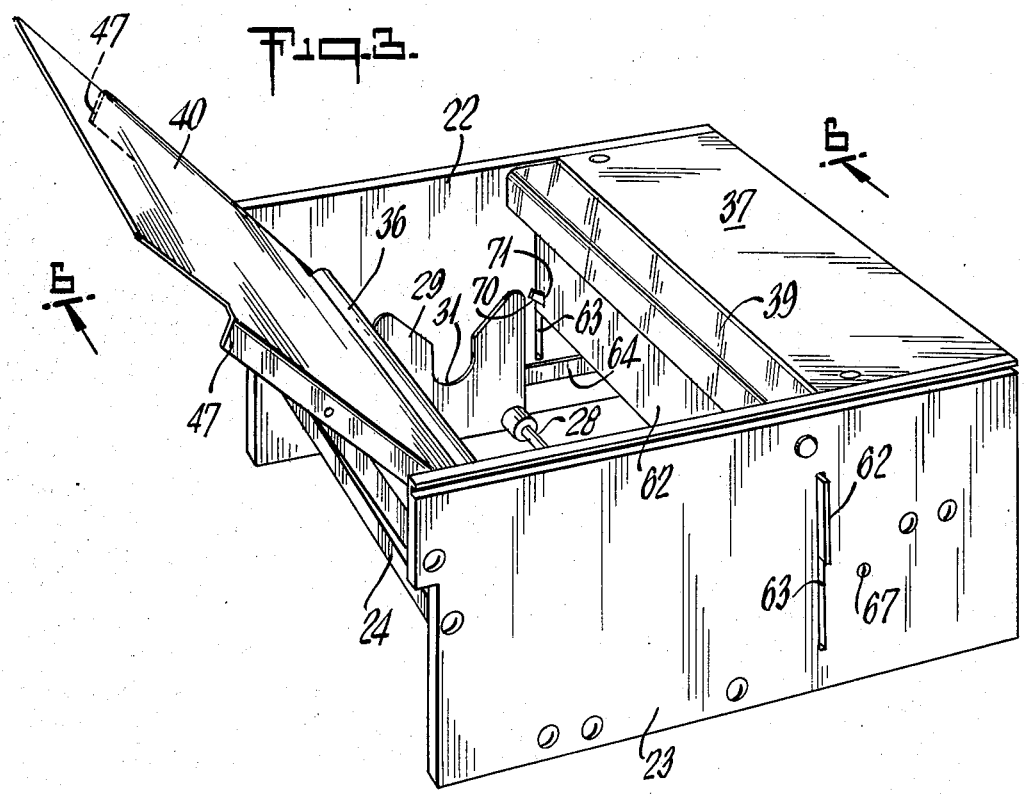

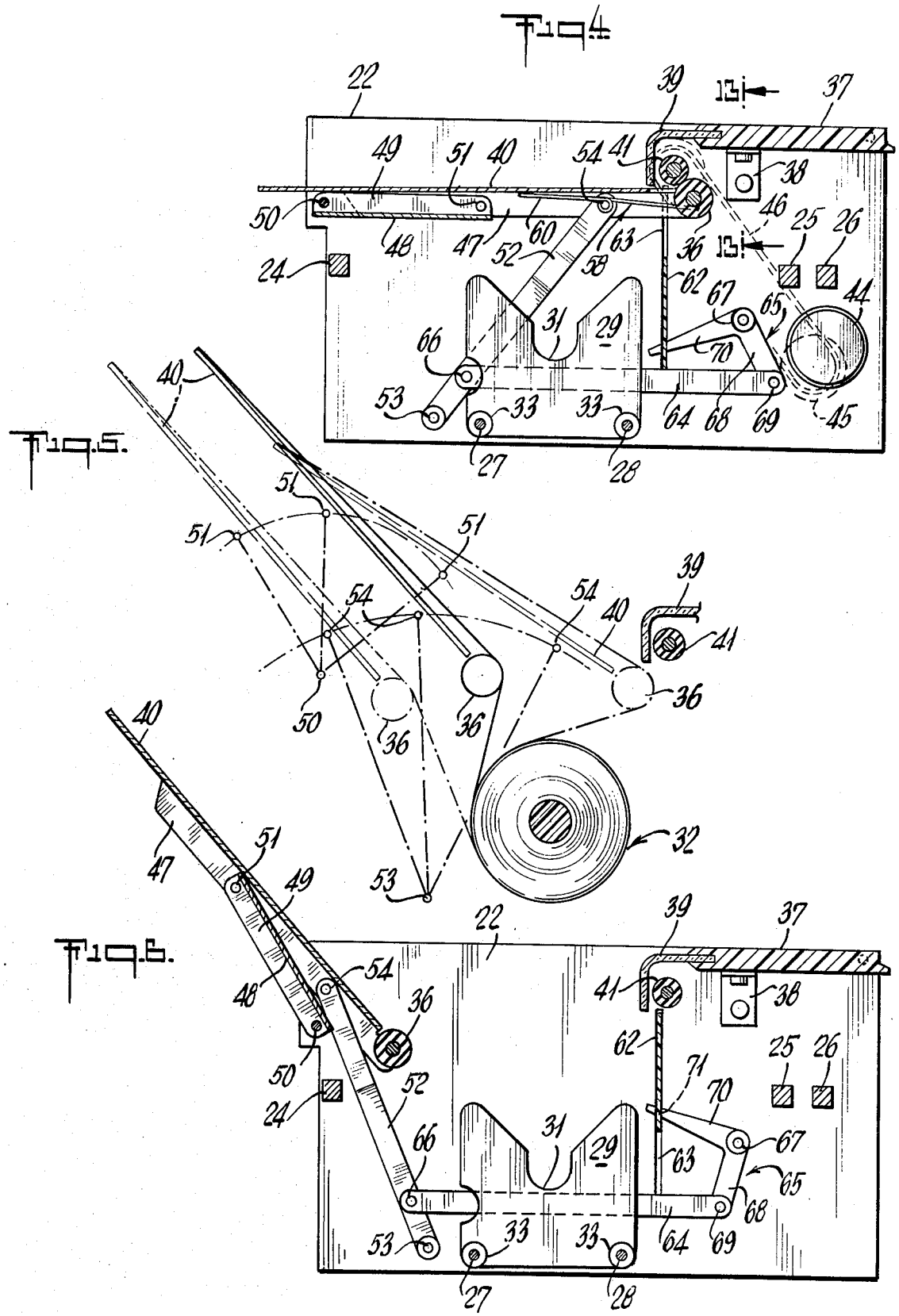

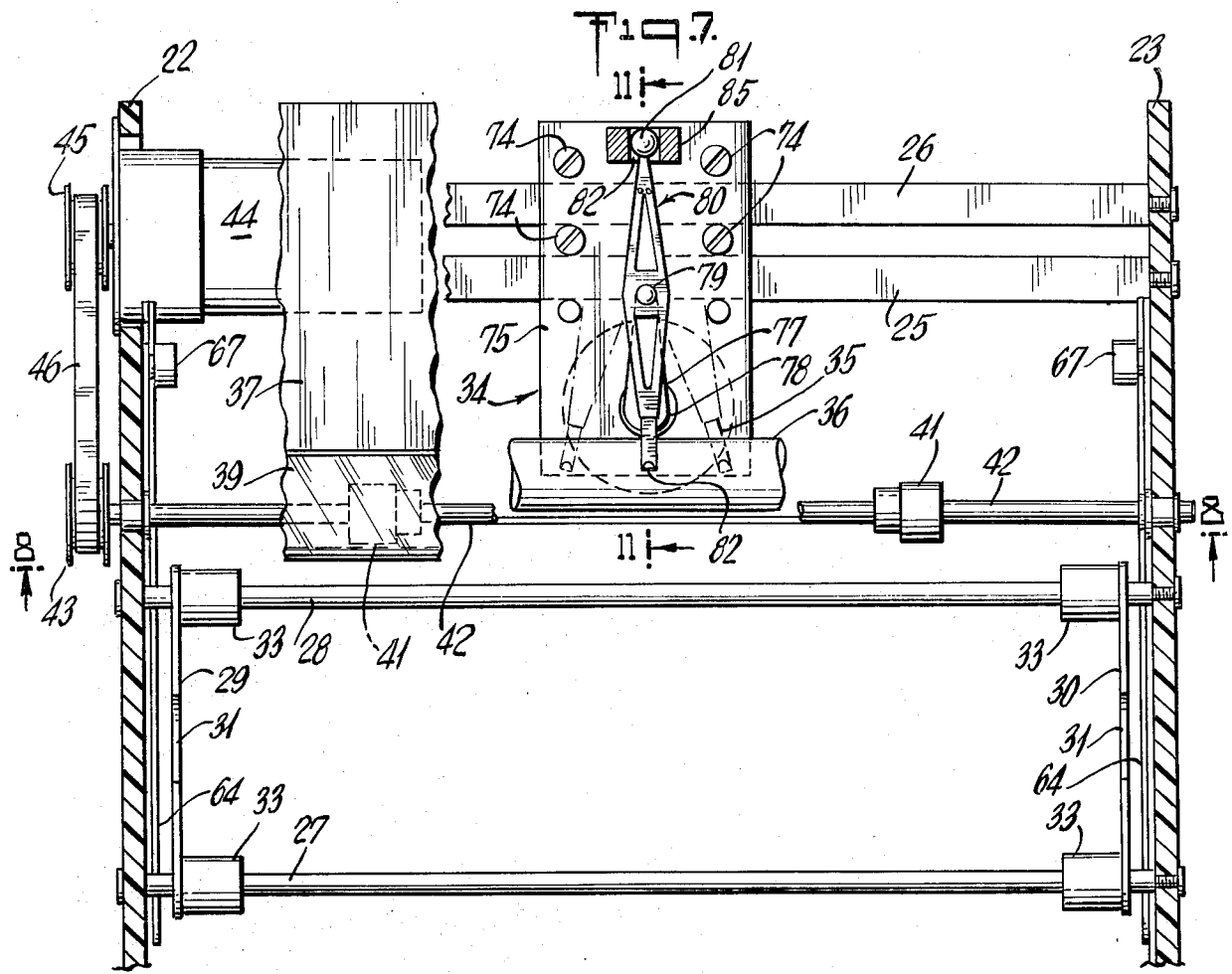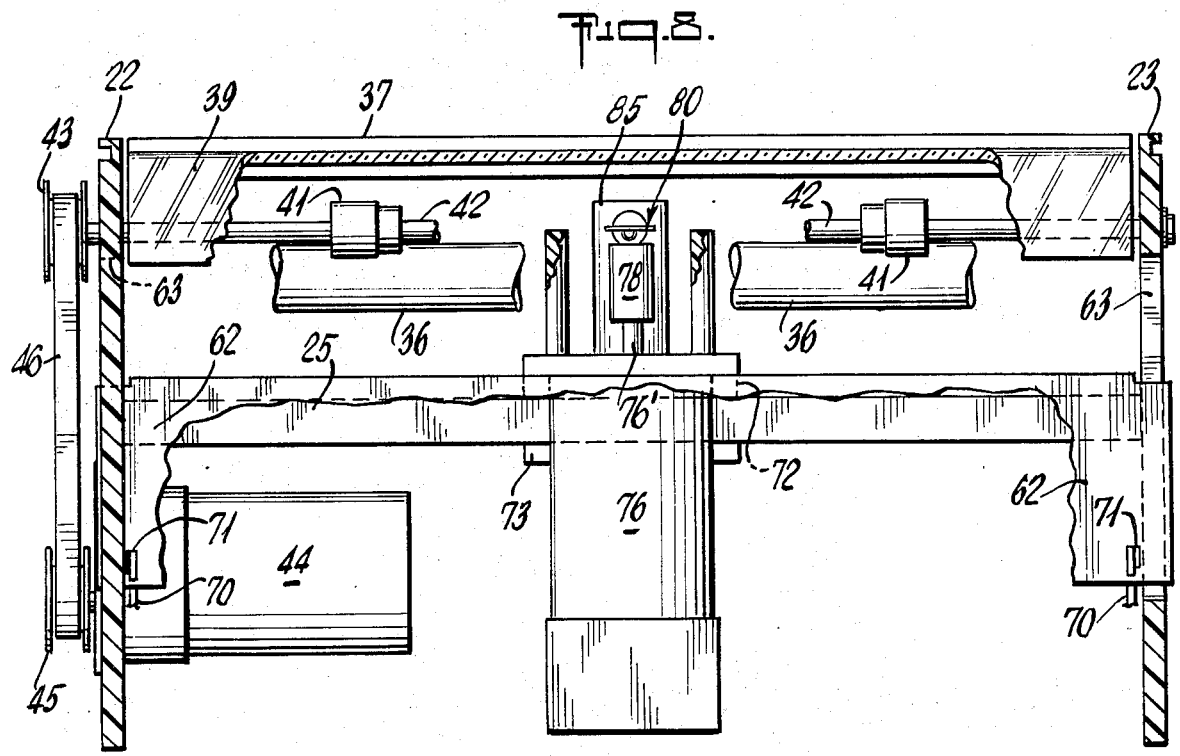

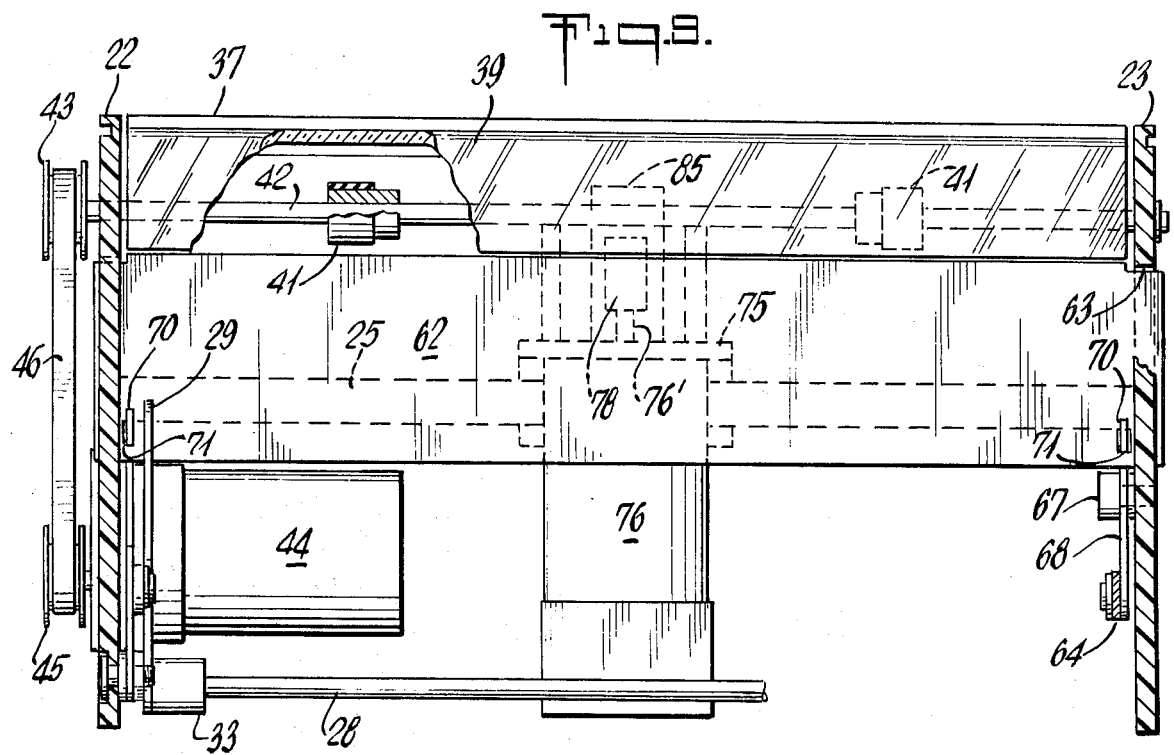
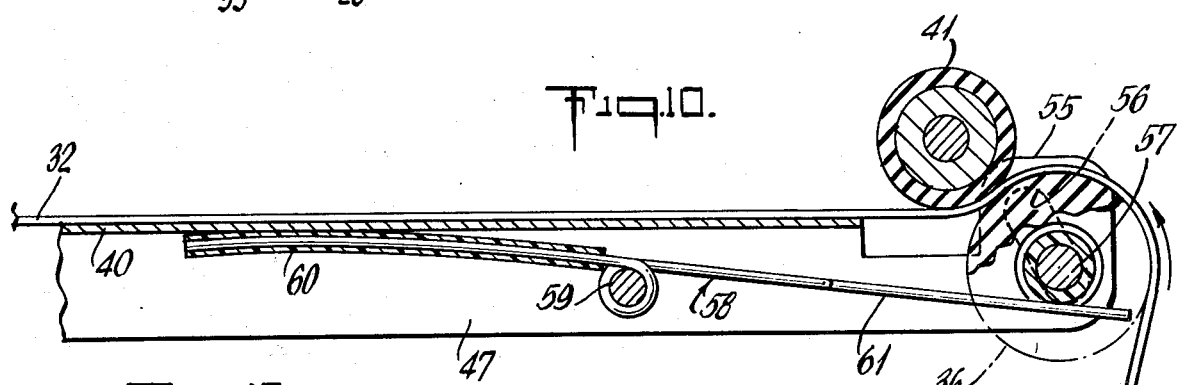
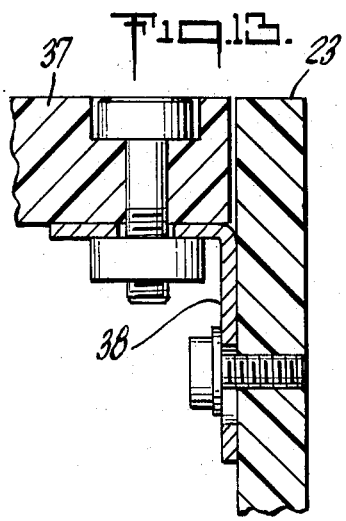
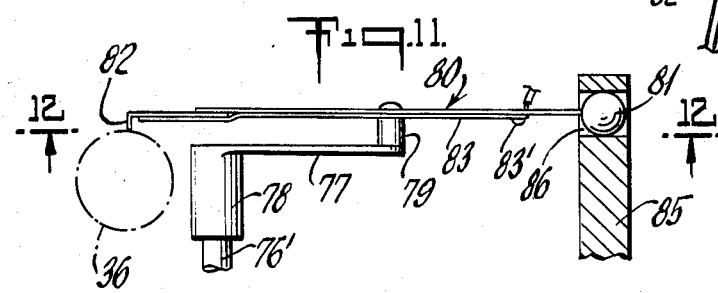
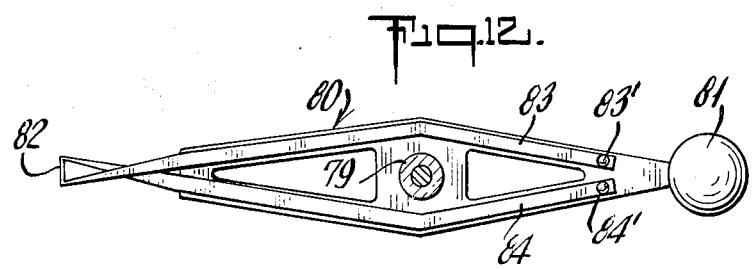

ELECTROCARDIOGRAPHIC APPARATUS WITH RECORDING PEN PROTECTOR

This invention relates to electrocardiographic apparatus and more specifically to a novel and improved housing for such apparatus and means for replacement of the recording paper which prevents the possibility of any electrical portions of the apparatus being accidentally connected directly or indirectly to ground.

It is recognized that in many applications wherein electrocardiographic apparatus is employed, it is essential that the equipment as well as the patient be completely isolated from ground and special transformers have been employed to provide power for the instrument which have negligible leakage currents. However, accidental contact with portions of the apparatus by an operator who may also be grounded can present a serious danger to the patient. One of the more prevalent instances wherein such accidental grounding can occur involves the replenishment of the recording paper or other recording medium while the patient is connected to the apparatus.

This invention provides a novel and improved arrangement of components which effectively prevents accidental grounding of any portion of the apparatus during normal operation or during replenishment of the recording medium so that danger to the patient is minimized if not effectively prevented.

Another object of the invention resides in the provision of a novel and improved electrocardiograph wherein all electrical components including metallic portions of the structure thereof are completely enclosed within a housing of insulated material and wherein means are included to close automatically a compartment containing recording pens when replenishing the recording medium.

Another object of the invention resides in the provision of a novel and improved pen recording structure wherein displaceable means are provided to facilitate insertion of a roll of recording material and wherein a barrier gate is automatically placed in a position shielding the recording pens during the actual process of inserting a roll of recording material.

A still further object of the invention resides in the provision of a novel and improved electrocardiograph wherein the possibility of accidentally grounding components of the actual apparatus is effectively reduced, if not completely avoided.

The foregoing objects and advantages of the invention are attained by housing the electrocardiographic apparatus within an insulated housing so that metal and other conductive portions cannot be accidentally contacted by an operator and wherein the actual recording means are automatically placed in a protected position during the replenishment of the recording medium.

The above and other objects and advantages of the invention will become more apparent from the following description and accompanying drawings forming part of this application.

In the drawings:

FIG. 1 is a perspective view of one embodiment of apparatus in accordance with the invention.

FIG. 2 is a perspective view of the apparatus for supporting and driving the recording paper and housing the recording pens which function to trace the electrocardiographic signals on the recording medium.

FIG. 3 is a perspective view of the apparatus illustrated in FIG. 2 in an open position to facilitate insertion of the recording medium.

FIG. 4 is a cross-sectional view taken along the line 4—4 of FIG. 2.

FIG.. 5 is a graphical illustration of the operation of the apparatus shown in FIG. 4 to facilitate insertion of the recording medium.

FIG. 6 is a cross-sectional view of FIG. 3 taken along the line 6—6 thereof.

FIG. 7 is a plan view of the structure shown in FIG. 2 with portions removed and broken away.

FIG. 8 is a cross-sectional view of FIG. 7 taken along the line 8—8 thereof.

FIG. 9 is a view similar to FIG. 8 with the barrier gate in a raised position.

FIG. 10 is an enlarged fragmentary portion of FIG. 4 illustrating the means for spring loading the platen roller to create pressure on the paper between it and the drive roller.

FIG. 11 is a cross-sectional view of FIG. 7 taken along the line 11—11 thereof to show the operation of one of the writing pens.

FIG. 12 is a cross-sectional view of FIG. 11 taken along the line 12—12 thereof; and FIG. 13 is a cross-sectional view of FIG. 4 taken along the line 13—13 thereof.

Referring now to the drawings and more specifically to FIG. 1, the electrocardiographic apparatus in accordance with the invention is generally denoted by the numeral 10 and includes a pair of end walls 11 and 12 supporting upper and lower cabinets 13 and 14 therebetween. For convenience, the apparatus is supported by wheels 15 and 16 and swiveled wheels 17. The electronic equipment comprising the actual electrocardiograph is contained within the cabinet 13 while the cabinet 14 contains the power supply for energizing the apparatus. The power supply is coupled to the apparatus by an insulated cable 18. The recording equipment comprising the motor driven pens, paper and paper feed is generally denoted by the numeral 19.

One form of electrocardiograph that may be utilized within the housing 13 is illustrated and described in U.S. Pat. No. 3,922,686 and the power supply would be mounted within the housing 14. The walls 11 and 12 of the apparatus 10 are formed of a suitable insulating material such as plastic, wood or the like. When utilizing wood, it may be preferable to utilize a plastic veneer on the surface thereof to facilitate cleaning and prevent absorption of moisture. Similarly the walls of the upper and lower housing portions 13 and 14 are also formed of a suitable insulating material and the cover of housing 13 is similarly formed of an insulating material. In this way, all of the metal portions of the actual electrocardiograph are completely protected. Similarly, the pushbutton controls 20 and the control knobs 21 are formed of plastic or other insulating material so that there is no possibility for an operator to accidentally ground any portion of the electronic circuitry. It will also be shown that the actual recording apparatus is similarly protected and embodies a novel and improved arrangement which permits insertion of recording paper while the apparatus is connected to a patient and without the danger of accidentally grounding the apparatus during that procedure.

Referring now to FIGS. 2 through 10, the recording apparatus generally denoted by the numeral 19 comprises a pair of side walls 22 and 23 preferably formed of a suitable insulating material of sufficient rigidity to support the operating elements disposed therebetween. The principal structural elements maintaining the side walls 22 and 23 in spaced relationship constitute the front transverse bar 24, a pair of rear transverse bars 25 and 26 and a pair of rods 27 and 28 at the lower edges of the said walls. The rods 27 and 28 also support a pair of plates 29 and 30 each having a V-shaped recess terminating in a circular portion 31 for receiving and holding a roll of paper such as that illustrated in FIG. 5 and denoted by the numeral 32. The supports 29 and 30 are adjustable on the rods 27 and 28 so that rolls of recording paper of different widths can be readily accommodated. This is attained by the utilization of short sleeves 33 secured to the supports 29 and 30 and slidably engaging the rods 27 and 28. The sleeves 33 can be fixed in position on the rods by tightening set screws (not shown) threadably engaging the sleeves.

The recorder 19 in the instant embodiment of the invention includes three motor driven recording pens generally denoted by the numeral 34 of which only one is illustrated in FIGS. 7 and 12. It will be observed, however, that the recording paper 32 shown in FIG. 1 has three traces 34a, 34b, and 34c. It is evident, therefore, that the recorder may embody any desired number of recording pens depending on the number of signals to be recorded simultaneously. Each pen assembly 34 is supported by the transverse rods 25 and 26 in a manner that will be described. For present purposes it need only be mentioned that the stylus 35 of each recording pen assembly 34 rides on a platen 36 about which the paper 32 passes as will be observed particularly in FIGS. 4, 5, and 6.

The recording pen assemblies 34 are protected by the top plate 37 of insulating material which is held in position between the side walls 22 and 23 by brackets 38 as shown in FIGS. 4, 6, and 13. Inasmuch as the structure of these brackets is self-evident, a detailed description is not considered necessary. The front portion of the top plate 37 carries an outwardly and downwardly extending member 39 also formed of insulating material. The member 39 extends downwardly into a position in spaced relationship to the plate 40 which supports the recording paper 32 after it has been recorded and as it is fed out of the recording assembly 19. It will be observed that when the plate 40 is in a horizontal position as shown in FIG. 4, the recording pens are completely protected and cannot be accidentally contacted by the operator. In this position the platen 36 carried by the inner edge of the plate 40 bears upwardly against a pair of drive rollers 41 carried by a transverse shaft 42, the latter having a drive pulley 43 on one end thereof. A motor 44 is carried by the side wall 22 and has a driving pulley 45 on the outer side of the wall 22. This driving pulley is coupled to the driven pulley 43 by a belt 46. In this way, pressure of the platen against the drive rollers 41 with the paper disposed therebetween, functions to automatically drive the paper when the plate 40 is in the position shown in FIG. 4.

The plate 40 which has depending side flanges 47 is carried by a transverse plate 48 having a pair of upwardly extending flanges 49 along each side edge thereof. As shown in FIG. 4, the forward edge of the plate 48 is pivotally carried by a transverse rod 50 extending between the side walls 22 and 23 with the flanges 49 lying to the inside of the flanges 47, the latter forming part of the plate 40. The righthand edge of each flange 49 of the plate 40 is pivoted at 51 to the flange 47 of the plate. In this way, as the plate is lifted to raise the front edge thereof as shown in FIGS. 5 and 6, the plate 48 pivots counter-clockwise to raise the front edge of the plate and at the same time displace the plate to the left as shown in FIG. 6. The rear edge of the plate 40 is supported by a pair of links 52 pivoted at their lower ends to the side walls 22 and 23 by pivots 53. The upper end of each link 52 is pivoted at 54 to the depending flange 47 of the top plate 40. In this way the plate 40 moves precisely through the path as illustrated in FIG. 5. To facilitate an understanding of the movement of the plate 40, reference is made specifically to FIGS. 4, 5, and 6. In FIG. 4 the plate is in a horizontal position while in FIG. 6 the plate is in the open inclined position to facilitate the insertion of the roll of recording paper. FIG. 5 shows the movement of the supporting elements for the plate 40, namely, the plate 48 and the links 52.

FIG. 10 illustrates the structure for supporting the platen 36 on the inner edge of the plate 40. It will be observed that the inner end of each flange 47 has an enlarged portion 55 having an inclined elongated slot 56. The shaft 57 supporting the platen 36 extends from the ends thereof and rotatably engages the slots 56. A spring 58 coiled about a post 59 has one end 60 bearing against the underside of the plate 40 while the end 61 bears against the shaft 57. As this spring arrangement is carried by both of the flanges 47 depending from the plate 40, the platen is normally urged upwardly against the drive rollers 41.

In order to prevent an operator from accidentally touching a recording pen assembly when the plate 40 is in a raised position as shown in FIG. 6 for the insertion of the roll of recording paper, a barrier plate 62 is provided to protect the recording pen assemblies. The barrier 62 is carried in slots 63 in the side walls 22 and 23 and is actuated by a pair of links 64 and a pair of bell cranks 65. Each link 64 is pivoted at 66 to its associated link 52 and at a point spaced from the pivot 53. The outer end of the arm 68 of bell crank 65 is pivoted at 69 to the link 64 while the other arm 70 of the bell crank 65 is tapered and engages a slot 71 near the lower edge of the barrier 62. With this arrangement and with the plate 40 as shown in FIG. 4, the link 64 is moved to the right and causes the bell crank 65 to move in a counter-clockwise direction thus lowering the barrier 62. When the plate 40 is raised to the position shown in FIG. 6 in order to insert a roll of recording paper, the link 64 moves to the left causing the bell crank 65 to rotate in a clockwise direction and raise the barrier 62 to prevent an operator from accidentally touching any of the recording assemblies. In this way all metal elements of the recording apparatus with the exception of the plate 40, which is insulated from the remainder of the apparatus, are protected at all times, and it is not possible to intentionally or accidentally ground any portion of the apparatus which is directly or indirectly connected to a patient.

The pen assemblies 34 of which only one is illustrated are carried by the transverse bars 25 and 26. More specifically and with reference to FIGS. 7 through 9, 11 and 12, a pair of plates 72 and 73 are secured to the bars by screws 74. The pen assembly is carried on a plate 75 and is driven by a motor 76 depending from the plate 75 and having a shaft 76' extending upwardly therefrom. An arm 77 is secured to the shaft by means of a sleeve 78 and the outer end of the arm 77 has a stud 79 pivotally engaging the pen 80. The righthand end of the pen 80 has a ball 81 slidably engaging an opening 86 in a vertically disposed post 85. The forward end of the pen 80 carries the nib 82 which rides on the platen 36. It will be observed that the pen 80 is of general diamond shape which provides longitudinal rigidity and also facilitates attachment of the conductors 83 and 84 along the outer edges thereof so that there is ample space for the pivot 79. The conductors are crossed at the forward end of the pen 80 and carry the nib 82. By applying a potential to the terminals 83' and 84', the nib 82 will be heated in order to effect the recording operation on the recording paper.

It will be observed in FIG. 11 that as the motor shaft 76 is rotated the nib 82 will move along a linear path on the platen 36 and in so doing the ball 81 will move horizontally, thereby effecting linear movement of the nib 82 on the platen 36.

The term "accidental grounding" as used in the specification and claims is intended to encompass any change in potential of the apparatus that may occur either by an operator touching metal parts thereof or by having any other conductive element contact metal parts of the apparatus.

While only one embodiment of the invention has been illustrated and described, it is understood that alterations, changes and modifications may be made without departing from the true scope and spirit thereof.

What is claimed is:

1. In electrocardiographic apparatus including means for amplifying and recording signals from a patient, a housing of insulating material wholly enclosing said amplifying means, recording means including a platen roller for retaining and feeding a recording medium about said roller, at least one pen having means for activating it in response to said signals for recording them on said medium as the latter passes over said platen roller, means for displacing said platen roller from engagement with said pen for replenishment of said medium and an insulating barrier movable to shield said pens from accidental grounding in response to the displacement of said platen roller.

2. In electrocardiographic apparatus according to claim 1 wherein each of said pen activating means comprises an elongated arm having a nib on one end thereof and a ball on the other end thereof, means having an opening therein slidably receiving said ball, a drive motor having a shaft movable through a predetermined arc in response to electrical signals to be recorded, said shaft being positioned at a point between the center of said arm and said nib, an arm carried by said shaft and pivoted to said arm at a point rearwardly of said shaft whereby movement of said shaft through said arc will cause said nib to move in a substantially linear path parallel to the axis of said platen roller.

3. In electrocardiographic apparatus according to claim 1 wherein said recording means includes a pair of spaced side walls, a plate disposed between said walls and carrying said platen roller on the inner end thereof, means carried by said side walls for holding a roll of recording material, means pivotally securing said plate to said side walls for movement from a horizontal position to an outer inclined position and exposing the last said means for replenishing said recording medium, and a linkage coupling said pivotal securing means to said insulating barrier to move said barrier upwardly when said plate is moved to the outer inclined position.

4. In electrocardiographic apparatus according to claim 3 wherein said side walls each include an elongated slot and said barrier in slidably retained in said slots.

5. In electrocardiographic apparatus according to claim 3 including a shaft having a pair of drive rollers rotatably carried by said side walls and means for rotating said shaft, said platen roller with the recording medium being disposed thereabout being urged against said drive rollers when said plate is in the horizontal position.

6. In electrocardiographic apparatus according to claim 5 wherein said platen roller is spring biased in an upwardly direction and against said drive rollers.

7. In electrocardiographic apparatus according to claim 6 wherein said plate is pivotally coupled to said side walls by a first pair of links each pivoted to one side of said plate at a point spaced from the platen roller and at the other end to said wall and by second linking means which lies in a horizontal plane with the plate in a horizontal position, the last said linking means being pivoted at the outer end to said walls and at the inner end to said plate.

8. In electrocardiographic apparatus according to claim 7 wherein said linkage coupling for moving said barrier comprises a pair of bell cranks pivoted to said side walls, each bell crank having one arm thereof engaging one end of said barrier and a link coupling the other arm thereof to one of said first pair of links.

* * * * *